United States Patent
Nascimento et al.

(10) Patent No.: US 10,669,509 B2
(45) Date of Patent: Jun. 2, 2020

(54) FRAGRANCE COMPOSITIONS AND AIR CARE DEVICES

(71) Applicants: RHODIA POLIAMIDA E ESPECIALIDADES S.A., São Paulo (BR); RHODIA OPERATIONS, Paris (FR)

(72) Inventors: Ronaldo Nascimento, São Paulo (BR); Darlene Felix, São Paulo (BR); Tingting Zhang, Shanghai (CN)

(73) Assignees: RHODIA OPERATIONS, Paris (FR); RHODIA POLIAMIDA E ESPECIALIDADES S.A., São Paulo (BR)

( * ) Notice: Subject to any disclaimer, the term of this patent is extended or adjusted under 35 U.S.C. 154(b) by 0 days.

(21) Appl. No.: 15/545,167

(22) PCT Filed: Jan. 25, 2016

(86) PCT No.: PCT/CN2016/072003
§ 371 (c)(1),
(2) Date: Jul. 20, 2017

(87) PCT Pub. No.: WO2016/119660
PCT Pub. Date: Aug. 4, 2016

(65) Prior Publication Data
US 2018/0320106 A1    Nov. 8, 2018

(30) Foreign Application Priority Data

Jan. 30, 2015 (WO) .................. PCT/IB2015/000097

(51) Int. Cl.
| | | |
|---|---|---|
| A61K 8/18 | (2006.01) |
| A61Q 13/00 | (2006.01) |
| A61K 8/00 | (2006.01) |
| C11B 9/00 | (2006.01) |
| A61L 9/03 | (2006.01) |
| A61L 9/04 | (2006.01) |
| A61L 9/12 | (2006.01) |

(52) U.S. Cl.
CPC .............. *C11B 9/0076* (2013.01); *A61L 9/03* (2013.01); *A61L 9/044* (2013.01); *A61L 9/127* (2013.01); *A61Q 13/00* (2013.01)

(58) Field of Classification Search
CPC . C11B 9/006; A61L 9/127; A61L 9/03; A61L 9/044; A61Q 13/00

USPC ...................................................... 512/25, 1
See application file for complete search history.

(56) References Cited

U.S. PATENT DOCUMENTS

| | | | |
|---|---|---|---|
| 1,994,932 A | 3/1935 | Vidal | |
| 2,597,195 A | 5/1952 | Smith | |
| 2,802,695 A | 8/1957 | Johnson | |
| 2,804,291 A | 8/1957 | Hard | |
| 2,847,976 A | 8/1958 | Spaulding | |
| 8,603,963 B1 | 12/2013 | Steward et al. | |
| 8,653,128 B1 | 2/2014 | Taneja | |
| 2009/0318326 A1* | 12/2009 | Lant ...................... | C11D 3/222 510/320 |
| 2013/0345107 A1* | 12/2013 | Son ...................... | C11D 3/2096 510/276 |
| 2015/0361281 A1* | 12/2015 | Nascimento ......... | C08G 18/542 252/364 |

FOREIGN PATENT DOCUMENTS

| | | | |
|---|---|---|---|
| CN | 104379118 A | 2/2015 | |
| DE | 102005056393 A1 | 5/2007 | |
| WO | 2013092962 A2 | 6/2013 | |
| WO | WO-2013092962 A2 * | 6/2013 | .............. A61K 8/345 |
| WO | WO-2014125357 A1 * | 8/2014 | ........... C08G 18/542 |
| WO | 2014187950 A1 | 11/2014 | |

OTHER PUBLICATIONS

First Office Action dated Jul. 3, 2019, issued in corresponding Chinese Patent Application No. CN-201680008141.5, with USPTO Global Dossier English translation (14 pages).
Extended European Search Report issued in European Application No. 16742722.8, dated Jul. 4, 2018 (7 pages).
"New fragrance compositions and air care devices", IP. com Journal, IP.com Inc., Feb. 3, 2015, IP.com No. IPCOM000240482D (12 pages).
"New Solvents for Solubilization of Fragrances in Candles", IP. com Journal, IP.com Inc., Aug. 24, 2015, IP.com No. IPCOM000242847D (3 pages).

* cited by examiner

*Primary Examiner* — Jessica Whiteley
(74) *Attorney, Agent, or Firm* — Osha Liang LLP

(57) ABSTRACT

The present invention aims a new fragrance composition comprising a fragrance compound and a solvent or carrier, wherein at least 10% by weight based on the total weight of solvent and carrier of the fragrance composition is one or more specific low vapor pressure volatile organic compound (VOC). The new fragrance composition is particularly well adapted to air care devices like wicking or electrical systems (plug-in, reed diffusers . . . ).

23 Claims, 5 Drawing Sheets

FIG 6 bis
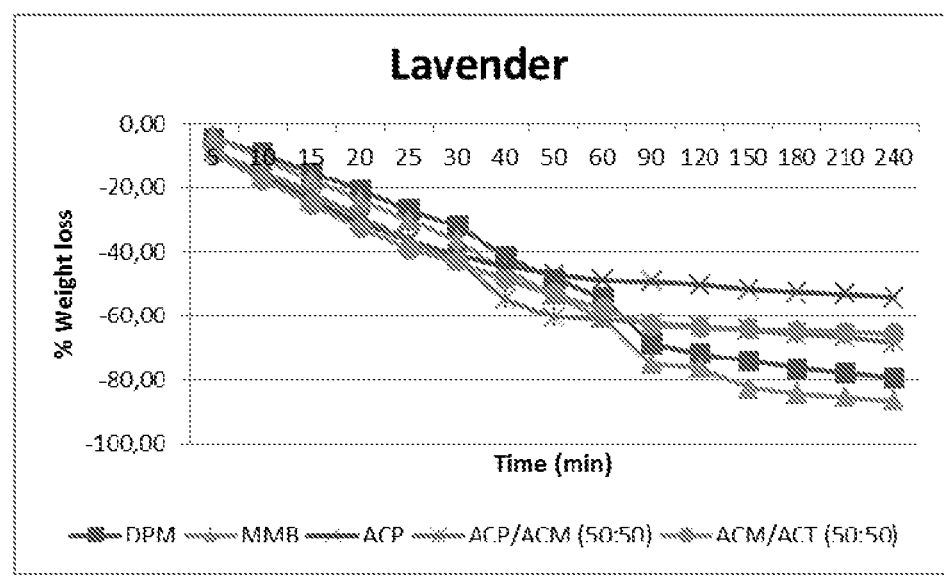

FRAGRANCE COMPOSITIONS AND AIR CARE DEVICES

CROSS-REFERENCE TO RELATED APPLICATION

This application is a U.S. national stage entry under 35 U.S.C. § 371 of International Patent Application No. PCT/CN2016/072003, filed Jan. 25, 2016, which claims priority to International Patent Application PCT/IB2015/000097 filed on Jan. 30, 2015, the whole content of each of these applications is hereby incorporated herein by reference for all purposes.

FIELD OF THE INVENTION

The present invention relates to a new fragrance composition containing low vapor pressure VOCs, as solvents and/or carriers, notably for use in air care devices.

BACKGROUND OF THE INVENTION

A problem in the area of air care devices is the uncontrolled "distillation" of fragrance components of differing volatilities, resulting in a variable fragrance profile over time, as perceived by the consumer. The use of carriers or solvents in fragrances aids in the uniform distribution or evaporation of these fragrance components and leads to a more homogeneous fragrance profile.

Many materials are used as carriers in air care devices including glycol ethers, isoparaffinic solvents (e.g., Isopar® solvents commercially available from ExxonMobil) and various branched esters. One problem associated with these materials is that many are classified as VOCs (volatile organic compounds). VOC's are increasingly of environmental and regulatory concern. There is one class of VOCs, low vapor pressure VOC's (LVP-VOCs), which are not as harmful to the atmosphere and are generally allowed under even the most stringent environmental regulations. This class of VOC has lower vapor pressure than regular VOCs as defined by standard definitions (e.g., <0.1 mm Hg at 20° C.).

The use of Dowanol DPMA (dipropylene glycol methyl ether acetate) has low vapor pressure VOC in fragrance composition is known from U.S. Pat. No. 8,603,963. However, it presents a very low evaporation rate (1.5, n-butyl acetate=100), it comes from petrochemical source and also presents a non-pleasure odor. In some devices, like reed diffusers, the odor of the solvent could be an issue since this can compete with the fragrance. Concerning the very low evaporation rate of Dowanol, it is also an issue in reed diffusers since the weight loss of the fragrance composition must be between 2.0-3.0 g/day to have a good spread in the environment.

Alkyl-4-hydroxymethyl-1,3-dioxolane molecules are known to be used in many different applications like coatings, paints, cleaning compositions, actives solubilization, because of their good solubilization properties, good physical-chemical properties, low odor and good HSE profile, that can replace products from petrochemical sources. However, those molecules have never been used is fragrance compositions, notably for air devices.

There is still a need for new fragrance compositions that have a reduced content of high vapor pressure VOCs. For example, there is a need for fragrance compositions whose solvents or carriers are mainly low vapor pressure VOCs, notably for use in liquid electrical air fresheners, such as a heated wick delivery systems, piezoelectrical spraying systems, electrospray devices, Venturi devices or wicking devices as reed diffusers. It is desired to provide fragrance compositions suitable for use in air fresheners that avoid the regulatory problems associated with many of the glycol ether compounds commonly found in liquid electrical air fresheners and reed diffusers. It is also desired to provide-fragrance compositions wherein the evaporation rate is regulated to within a predetermined period of time (e.g., 30 days, or 40 days, or 60 days), during which at least substantially all of the fragrance is effectively evaporated into the surrounding environment, preferably in a controlled fashion.

It is thus an object to provide fragrance compositions that contain mainly low pressure VOCs, as solvents or carriers that are economical to produce and have good safety characteristics, including low toxicity and low flammability. Advantageously it is an object to provide such fragrances compositions wherein the low vapor pressure VOCs, used as solvents or carriers are synthesized from renewable sources.

Another and related object of the invention is to provide fragrance compositions that contain essentially low pressure VOCs, as solvents or carriers having a controllable evaporation rate and that are suitable for use in, for example, a wick type air fragrance dispenser (air freshener) like reed diffusers. More specifically, it is an object of the invention to provide a controllable evaporation rate and permit effective utilization of the fragrance composition in a liquid electrical air freshener dispenser and/or in wick devices like reed diffusers.

SUMMARY OF THE INVENTION

The present invention provides a new fragrance composition that fulfills at least one of the requirements described above. Indeed, surprisingly, it has been found that the use of one or more alkyl(or aryl)-4-hydroxy(or alkoxy)methyl-1,3-dioxolane molecules or esters thereof as solvent or carrier in combination with a fragrance component allows to maintain the volatility of such a fragrance compound so that the composition performs properly in an electrical liquid air freshener device or in a wick device like a reed diffuser. Those molecules, besides the ability to solubilize the fragrance, also present a low odor.

In particular, the invention concerns fragrance composition comprising a fragrance compound and a solvent or carrier, wherein at least 10% by weight based on the total weight of solvent and carrier of the composition, is at least one compound of formula I below:

wherein $R_1$ and $R_2$, independently from one another, are selected in the group consisting of: a linear or branched C1-C12 alkyl, a C4-C12 cycloalkyl or an aryl.

$R_3$ is H, a linear or branched alkyl, a cycloalkyl or a —C(=O)$R_4$ group, with $R_4$ being a linear or branched alkyl or cycloalkyl.

Indeed, ketal-type molecules of formula I like solketal, present a suitable evaporation profile in order to deliver the fragrance in a constant rate during the lifetime of the application, like reed diffusers, electrical plug-ins, etc. In addition, those molecules are synthesized from renewable source, like glycerol (co-product from biodiesel production).

In other words, the present invention aims at the use of at least one compound of formula I below:

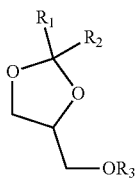

(I)

wherein $R_1$ and $R_2$, independently from one another, are selected in the group consisting of: a linear or branched C1-C12 alkyl, a C4-C12 cycloalkyl or an aryl.

$R_3$ is H, a linear or branched alkyl, a cycloalkyl or a —C(=O)$R_4$ group, with $R_4$ being a linear or branched alkyl or cycloalkyl as solvent or carrier in a fragrance composition comprising at least a fragrance compound, wherein the compound of formula I represents at least 10% by weight based on the total weight of solvent and carrier of the composition.

The present invention also aims an air care device comprising the fragrance composition as defined above, the air care device being a wicking device, an electrical device or an aerosol device.

In other words, the present invention concerns the use of a fragrance composition comprising a fragrance compound and a solvent or carrier, wherein at least one compound of formula I is present in an amount of at least 10% by weight based on the total weight of solvent and carrier of the composition in an air care device, the air care device being a wicking device, an electrical device or an aerosol device.

A third aspect of the invention is a method of decreasing the amount of high vapor pressure VOC solvent in a fragrance composition. This method includes removing at least a portion of any high vapor pressure VOC present in the composition (preferably the entire amount of high vapor pressure VOC present), adding at least 10% by weight based on the total weight of solvent and carrier of the composition, of at least one compound of formula I described above to the composition.

DETAILED DESCRIPTION

As used herein, a "low vapor pressure VOC" or "LVP-VOC" refers to organic solvents or carriers for use in a consumer product containing fragrance materials that have a vapor pressure of less than (<0.1 mm Hg at 20° C.).

As used herein, a "high vapor pressure VOC" or "HVP-VOC" refers to organic solvents or carriers for use in a consumer product containing fragrance materials that have a vapor pressure greater than or equal to (≥)0.1 mm Hg at 20° C.

As used herein, the term "solvent" and "carrier" are used interchangeably and, unless specified otherwise, are generally mentioned with respect to a low vapor pressure VOC or high vapor pressure VOC.

Unless specified otherwise, all vapor pressures listed in this disclosure are the vapor pressure at 25° C. It is noted, however, that the HVPVOC and LVPVOC vapor pressures are specified at 20° C., in accordance with the convention established by the California Air Resources Board (CARB).

Term "a" should be considered as a singular or a generic plural all along the present specification, except otherwise specified.

Compound of Formula I

According to the present invention, at least one compound of formula I described above is present as a LVP-VOC (solvent or carrier) in the fragrance composition.

In this formula I, it is preferred that $R_1$ and $R_2$, independently from one another, are selected in the group consisting of: methyl, ethyl, isopropyl, n-propyl, isobutyl, n-butyl, tert-butyl, n-pentyl, cyclopentyl, cyclohexyl or phenyl.

In the above formula I, $R_3$ is advantageously H or a —C(=O)$R_4$ group, with $R_4$ being methyl, ethyl, isopropyl, n-propyl, isobutyl, n-butyl or tert-butyl.

One preferred embodiment is when $R_1$ and $R_2$ are methyl and $R_3$ is H. In this case, the compound is commercially available, for example under the name Augeo® Clean Multi or Solketal. This compound can be synthesized by reaction between glycerol and acetone, under well-known classical conditions.

In another embodiment, $R_1$ is methyl, $R_2$ is isobutyl and $R_3$ is H. In this case, the compound is commercially available, for example under the name Augeo® Clean Plus. This compound can be synthesized by reaction between glycerol and methyl-isobutyl ketone, under well-known classical conditions.

In a third embodiment, $R_1$ is methyl, $R_2$ is phenyl and $R_3$ is H. In this case, the compound is commercially available, for example under the name Augeo® Film HB. This compound can be synthesized by reaction between glycerol and acetophenone, under well-known classical conditions.

Glycerol can be obtained as a coproduct from biodiesel production during the transesterification of triglycerides.

Another possibility is to have $R_1$ and $R_2$ are methyl and $R_3$ is a —C(=O)$R_4$ group, with $R_4$ being methyl. In this case, the compound is commercially available, for example under the name Augeo® ACT. This compound can be synthesized by transesterification of Solketal with an alkyl acetate under well-known classical conditions.

In a particular embodiment of the present invention, the fragrance composition comprises, as solvent or carrier a blend of two or more compounds of formula I.

Advantageously, said blend of two or more compounds of formula I comprises the following compounds 1.1 and 1.2:

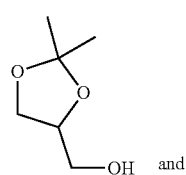

(I.1)

and

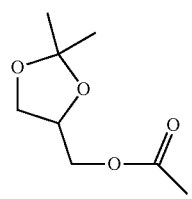

(I.2)

Said blend, e.g Augeo® Clean Multi: Augeo® ACT can be in the following proportions 95:5-5:95, preferably 90:10-10-90.

According to the invention, in the fragrance composition described above, the at least one compound of formula I represents at least 20% by weight based on the total weight of solvent and carrier of the fragrance composition, preferably at least 40% by weight, more preferably at least 60% by weight.

In a particular embodiment, the compound of formula I can represent 100% by weight based on the total weight of solvent and carrier of the fragrance composition.

Fragrance Compound

The fragrance composition includes a fragrance compound. This compound can be selected from primary alcohols, secondary alcohols, aldehydes, esters, ketones, phenolic compounds, terpenes and other recognized aromachemical compounds.

As used herein, the term "fragrance compound" refers to components that impart a generally hedonically pleasing fragrance. In one embodiment, fragrance components refer to fragrance and flavor materials listed in either Allured's Flavor and Fragrance materials 2004, published by Allured Publishing Inc., the IFRA (International Fragrance Research Association) database, and RIFM (Research Institute of Fragrance Materials) database, each of which and hereby incorporated by reference in their entirety.

The fragrance compound according to the invention is advantageously a commercial fragrance (e.g., citric like, lavender like and vanilla like).

In the fragrance composition of the invention, the fragrance compound can represent from 10 to 80% by weight based on the total weight of the fragrance composition, advantageously from 20 to 60% by weight based on the total weight of the fragrance composition.

Other Components

The fragrance composition of the invention can comprise other components like water, surfactants, colorants, potentiators, etc. Generally, the total amount of those other components do not exceed 40% by weight based on the total weight of the composition, preferably less than 20% by weight.

In one embodiment, one or more potentiator compound(s) are represented by the formula:

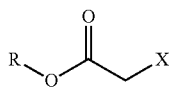

wherein
R is a $C_1$-$C_{10}$ substituted or unsubstituted alkyl, alkenyl group, or a $C_4$-$C_8$ substituted or unsubstituted cycloalkyl or aryl group; and X is hydrogen, or a $C_1$-$C_5$ unsubstituted alkyl group.

In one embodiment, R is a $C_4$-$C_8$ substituted or unsubstituted alkyl group. In one embodiment, R is a $C_6$ substituted or unsubstituted alkyl group. R can be substituted, for example, anywhere along the chain with one or more methyl groups. In one embodiment, X is H. In one embodiment, X is $C_1$-$C_3$ unsubstituted alkyl group.

In one embodiment, the potentiator compound is selected from hexyl acetate, 3,3,5-trimethylhexyl acetate, bornyl formate, 3-hexenyl butyrate, phenyl ethyl acetal, butyl hexanoate, isononanol, acetone alcohol, isoprenyl acetate, isobutyl 2-pentanoate, amyl propionate, herbal dioxane, furfuryl formate, methyl acetyl acetone, and butyl acetoacetate. In one embodiment, the potentiator compound is selected from 3,3,5-trimethylhexyl acetate and hexyl acetate.

Air Care Devices

As mentioned above, the present invention also aims an air care device comprising the fragrance composition as defined above, the air care device being a wicking device, an electrical device or an aerosol device.

The term "air care device" includes any suitable surface that allows for at least some evaporation of volatile materials. Any suitable air care device having any suitable size, shape, form, or configuration can be used. Suitable air care devices can be made from any suitable material, including but not limited to: natural materials, man-made materials, fibrous materials, non-fibrous materials, porous materials, non-porous materials, and combinations thereof. In certain embodiments, the air care devices used herein are flameless in character and include any device used for dispensing any type of volatile material (e.g. liquids) into the atmosphere (such as fragrance, deodorant, disinfectant or insecticide active agent). In certain non-limiting embodiments, a typical air care device utilizes a combination of sticks, wick, gel, and/or porous surface, and an emanating region to dispense a volatile liquid from a liquid fluid reservoir.

Air care devices (such as wicking devices) are known for dispensing volatile liquids into the atmosphere, such as fragrance, deodorant, disinfectant or insecticide active agent. A typical air care device utilizes a combination of a wick and emanating region to dispense a volatile liquid from a liquid fluid reservoir. Air care devices are described in U.S. Pat. Nos. 1,994,932; 2,597,195; 2,802,695; 2,804,291; 2,847,976. Ideally, the air care device should require little or no maintenance and should perform in a manner that allows the volatile material to be dispensed at a steady and controlled rate into the designated area while maintaining its emission integrity over the life span of the device.

In one embodiment, the air care device is an electrical liquid air freshener device. As noted above, the term "electrical liquid air freshener device" or "liquid electrical air freshener" refers to device or system that includes an electrical or battery operated source of energy which includes heated liquid wick delivery systems, piezoelectrical spraying systems, electrospray devices or Venturi devices. Commercial examples of electrical liquid air freshener devices include, but are not limited to, Glade® PlugIns® Scented oil, sold by SC Johnson & Sons; Air Wick Scented Oils, and Air Wick X-Press® Scented Oils, sold by Reckitt Benckiser; Febreze Noticeables sold by Procter & Gamble Co., Electric Home Air Fresheners, sold by the Yankee Candle Co.; and Renuzit Scented Oils, sold by Henkel AG.

Advantageously, the air care device can be an electrical liquid air freshener.

As used herein, the term "electrical liquid air freshener device" refers to device or system that includes an electrical or battery source of energy. The term "electrical liquid air freshener device includes heated liquid wick systems, piezoelectrical spraying systems, electrospray devices and Venturi devices, as well as devices that are powered by solar or other alternative forms of energy.

The electrical liquid air freshener is preferably a plug-in.

The presently disclosed fragrance composition can be in the form of a simple mixture of liquid fragrance components and LVP-VOC solvents, or can be in an encapsulated form, e.g., entrapped in a solid matrix that may include wall-forming and plasticizing materials such as mono-, di- or trisaccharides, natural or modified starches, hydrocolloids, cellulose derivatives, polyvinyl acetates, polyvinylalcohols, proteins or pectins. Examples of particularly useful matrix materials include, for example, sucrose, glucose, lactose, levulose, fructose, maltose, ribose, dextrose, isomalt, sorbitol, mannitol, xylitol, lactitol, malitol, pentatol, arabinose, pentose, xylose, galactose, maltodextrin, dextrin, chemically modified starch, hydrogenated starch hydrolysate, succinylated or hydrolysed starch, agar, carrageenan, gum arabic, gum accacia, tragacanth, alginates, methyl cellulose, carboxymethyl cellulose, hydroxyethyl cellulose, hydroxypropylmethyl cellulose, derivatives, gelatin, agar, alginate and mixtures thereof. Encapsulation techniques are well-known to persons skilled in the art, and may be performed, for instance, using techniques such as spray-drying, agglomeration or extrusion, or coating encapsulation, including coacervation and complex coacervation techniques.

Alternatively, the air care device can be a wicking device.

As used herein, the term "wick device" refers to device or system that doesn't include an electrical or battery source of energy. The term "reed diffuser" is applied for wick type devices that use the principle of capillarity of the formula that evaporates through the sticks.

In one embodiment, the wick device is a reed diffuser. As noted above, the term "reed diffuser" refers to device or system that does not include an electrical or battery operated source of energy, but this type of devices uses the principle of capillarity of the formula that evaporates through the sticks. Commercial examples of reed diffuser devices include, but are not limited to, Glade® PlugIns® Scented oil, sold by SC Johnson & Sons; Air Wick Scented Oils, and Air Wick X-Press® Scented Oils, sold by Reckitt Benckiser; Febreze Noticeables sold by Procter & Gamble Co., Electric Home Air Fresheners, sold by the Yankee Candle Co.; and Renuzit Scented Oils, sold by Henkel.

When the air care device is an aerosol device, a propellant is introduced into the container, with the fragrance composition.

Performances

In one embodiment, at least 10% of the fragrance composition, by weight, evaporates within 30 days for a reed diffuser, of being maintained at ambient conditions. Preferably, the fragrance composition evaporates in a controlled fashion. The evaporation rate can be tailored to suit the evaporation rate desired in the particular application.

As used herein, a fragrance composition evaporates in a controlled fashion when the evaporation rate, measured as weight of fragrance loss, per unit of time (e.g, 0.2-3.0 g/day) over a given time period (e.g., 30 days) is relatively constant over the given time period. In one embodiment, the evaporation rate is relatively constant when the weight of fragrance loss per unit of time differs by less than ±5%, or ±10% or ±20% over the given time period.

Low Vapor Pressure VOCs

As noted above, as used herein, a "low vapor pressure VOCs" or "LVP-VOC" refers to organic solvents or carriers that have a vapor pressure of less than (<) 0.1 mm Hg at 20° C. Low vapor pressure VOCs, such as compounds of formula I described above, have not been recognized and widely used, if at all, in liquid electrical air fresheners or wick devices as reed diffusers. When low vapor pressure VOCs are employed, the resulting fragrance composition achieves performance that meets or exceeds the performance of comparable formulations that contain higher vapor pressure VOCs that are subject to increasingly stringent environmental regulation. These formulas are advantageous in that they can be fragranced with a low and/or pleasant fragrance profile and have a good weight loss profile, as well as, low toxicity issues and none of the VOC problems associated with other carriers that are typically used in air care applications.

One example is Augeo Clean Multi that has a vapor pressure of 0.04 mmHg at 20° C.

It has surprisingly been found that the fragrance composition can yield hedonically pleasing and constant fragrance profiles when used in an electrical liquid air freshener or a wick device such as reed diffusers. Thus, one embodiment of the presently disclosed subject matter provides a wick device (e.g., reed diffuser) that contains the fragrance composition disclosed herein.

The evaporation rate of the fragrance compound(s) can be controlled to dispense the fragrance into the surrounding environment over extended periods of time. The perfumer of ordinary skill can modify the fragrance composition to provide controlled evaporation into small (e.g., a bath or living room) or large areas (e.g., large commercial and recreational spaces). In one embodiment, the presently disclosed fragrance compositions evaporate in a controlled fashion. A fragrance composition evaporates in a controlled fashion when the evaporation rate, measured as weight of fragrance loss, per unit of time (e.g, 0.2-3.0 g/day) over a given time period (e.g., 30 days) is relatively constant over the given time period. In one embodiment, the evaporation rate is relatively constant when the weight of fragrance loss per unit of time differs by less than ±5%, or ±10% or ±20% over the given time period.

In one embodiment, the presently disclosed fragrance composition evaporates at a rate of from about 0.2 to about 3.0 grams per day, over 30 days. In a still further embodiment, the evaporation rate (e.g., grams of fragrance lost per day), over a given time period (30, 40 or 60 days for example) varies by less than ±5%, or ±10% or ±20% over the given time period.

BRIEF DESCRIPTION OF THE DRAWINGS

For a more complete understanding of various embodiments of the described subject matter and its advantages, reference is now made to the following description, taken in conjunction with the accompanying drawings, in which:

FIG. 3bis is an evaporation comparison among Low VOC carrier formulations C4, C5, and C6, as described below in Example 3, measured as the amount of weight loss of vanilla fragrance over 50 hours.

FIG. 4bis is an evaporation comparison among Low VOC carrier formulations D5, D6, D7, D8, D9, and D10, as described below in Example 4, measured as the amount of weight loss of lavender fragrance over 240 minutes.

FIG. 6*bis* is an evaporation comparison among Low VOC carrier formulations F6, F7, F8, F9, and F10, as described below in Example 6, measured as the amount of weight loss of lavender fragrance over 240 minutes.

EXAMPLES

The present application is further described by means of the examples, presented below, wherein the abbreviations have the usual meaning in the art.

Methodology to Measure Evaporation Rate

Weigh a Petri Dish of surface area around 70 cm2=$PD_{initial}$

Weigh 1 g of the formulation at the Peri Dish=$F_{initial}$

Leave the Petri Dish at room temperature (around 25° C.) and controlled humidity Weigh (Petri Dish+formulation) every 30 minutes during at least 8 hours=$(PD+F)x$, when x is each point of weighting Calculate the loss of weight for each point:

$$\% \text{ Weight Loss} = \frac{[(PD_{initial} + F_{initial}) - (PD+F)_x] \times 100}{(PD_{initial} + F_{initial})}$$

Example 1

A commercially-available lavender fragrance composition that contains Dowanol DPM Glycol Ether (A2) is compared to the same composition wherein the solvent or carrier has been 100% replaced by Augeo® Clean Multi (A1).

Dowanol DPM Glycol Ether, which is HVP-VOC, may not comply with the strictest environmental regulations, such as the regulations established by the California Air Resource Board (CARB).

A formulation with a similar evaporation rate, and olfactive properties as the formulations containing HVP-VOCs is desired, yet using a low vapor pressure VOC solvent that complies with the strictest regulatory standards, (e.g., is CARB compliant).

Formulation (A1) and Comparative formulation (A2) are described below in Table 1:

TABLE 1

Fragrance Composition for a Reed Diffuser (Wick Device Type).

| Components | A1 % w/w | A2 % w/w |
|---|---|---|
| Fragrance | 20 | 20 |
| Augeo Clean Multi | 60-80 | 0 |
| Dowanol DPM (Glycol ether) | 0 | 60-80 |
| Other Components | 5-20 | 5-20 |

Figure 1:
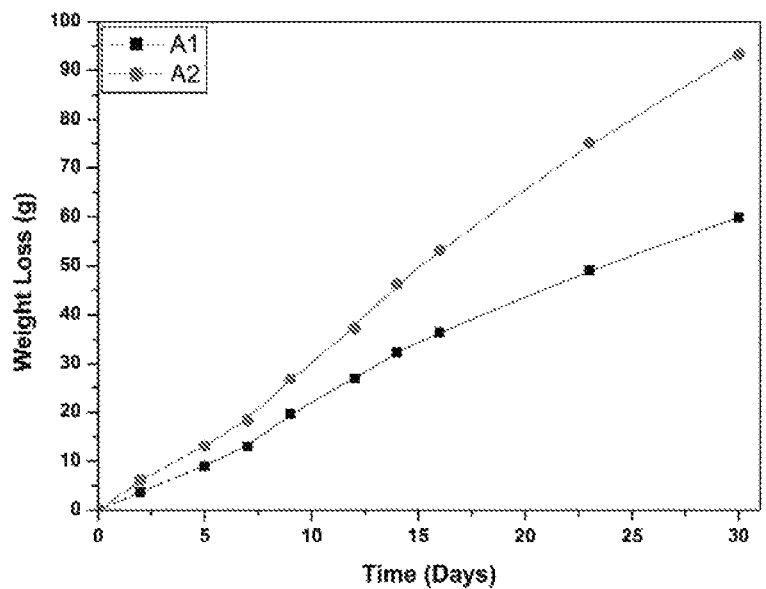
FIG. 1 is an evaporation comparison between the standard fragrance formulation A2 (DPM), and the Low Vapor Pressure VOC formulation A1 according to the invention, as described below in Example 1, measured as the amount of weight loss of fragrance over 30 days.

Evaporation curves for Comparative Formulation A2 and Formulation A1 are shown in FIG. 1, measured as the amount of weight loss of the composition. As shown therein, evaporation profile of the Low VOC Carrier Formulation A1 over 30 days is similar to and even better than that of Comparative Formulation A2, which is not compliant with the regulations established by the California Air Resource Board (CARB). Indeed, Formulation A1 evaporates slower than A2, which means the solvent is able to carry the fragrance into the air for a longer period of time, showing better performance.

Example 2

A commercially-available lavender fragrance composition that contain Methoxy methyl butanol (MMB)(B2) is compared to the same composition wherein the solvent or carrier has been 100% replaced by Augeo® Clean Multi (B1).

Methoxy methyl butanol (MMB), which is HVP-VOC may not comply with the strictest environmental regulations, such as the regulations established by the California Air Resource Board (CARB).

A formulation with a similar evaporation rate, and olfactive properties as Comparative Formulation B2 is desired, yet using a low vapor pressure VOC solvent that complies with the strictest regulatory standards, (e.g., is CARB compliant).

Formulation (B1) and Comparative formulation (B2) are described below in Table 2:

TABLE 2

Fragrance Composition for a Reed Diffuser (Wick Device Type).

| Components | B1 % w/w | B2 % w/w |
|---|---|---|
| Fragrance | 20 | 20 |
| Augeo Clean Multi | 60-80 | 0 |
| Methoxy methyl butanol | 0 | 60-80 |
| Other Components | 5-20 | 5-20 |

Figure 2:
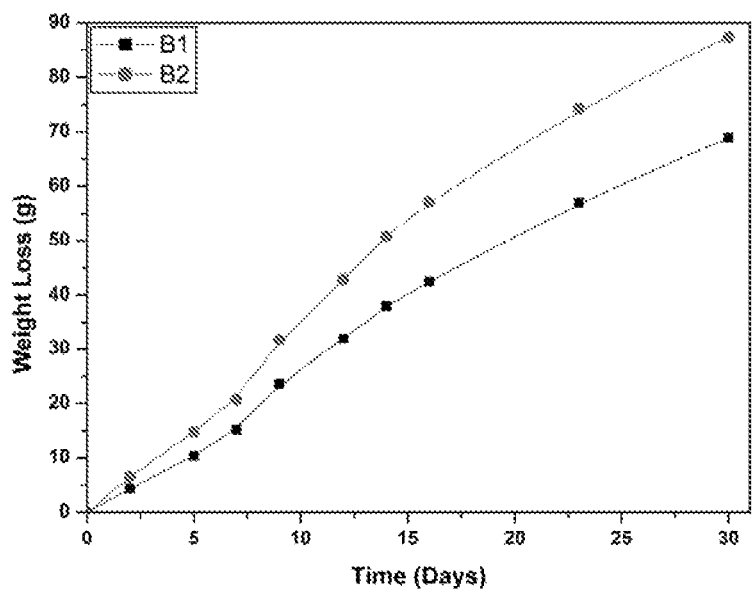
FIG. 2 is an evaporation comparison between the standard fragrance formulation B2 (MMB), and the Low Vapor Pressure VOC formulation B1 according to the invention, as described below in Example 2, measured as the amount of weight loss of fragrance over 30 days.

Evaporation curves for Comparative Formulation B2 and Low VOC Carrier Formulation B1 are shown in FIG. 2, measured as the amount of weight loss of the composition. As shown therein, evaporation profile of the Low VOC Carrier Formulation B1 over 30 days is similar to and even better than that of Comparative Formulations B2, which is not compliant with the regulations established by the California Air Resource Board (CARB). As for example 1, the evaporation for formulation B1 is slower than B2, which means the fragrance remains in the air for a longer period of time.

Example 3—Solvent Based Fragrance Compositions

Commercially-available fragrances are solubilized into the solvents described below in Table 3, and the evaporation rate is measured.

TABLE 3

Fragrance Composition for a Reed Diffuser (Wick Device Type).

| Components | C1 % w/w | C2 % w/w | C3 % w/w | C4 % w/w | C5 % w/w | C6 % w/w |
|---|---|---|---|---|---|---|
| Fruit Fragrance | 8 | 8 | 8 | 0 | 0 | 0 |
| Vanilla Fragrance | 0 | 0 | 0 | 8 | 8 | 8 |
| Augeo Clean Multi | 92 | 0 | 0 | 92 | 0 | 0 |
| Dowanol DPM (Glycol ether) | 0 | 92 | 0 | 0 | 92 | 0 |
| Methoxy methyl butanol | 0 | 0 | 92 | 0 | 0 | 92 |

Figure 3:
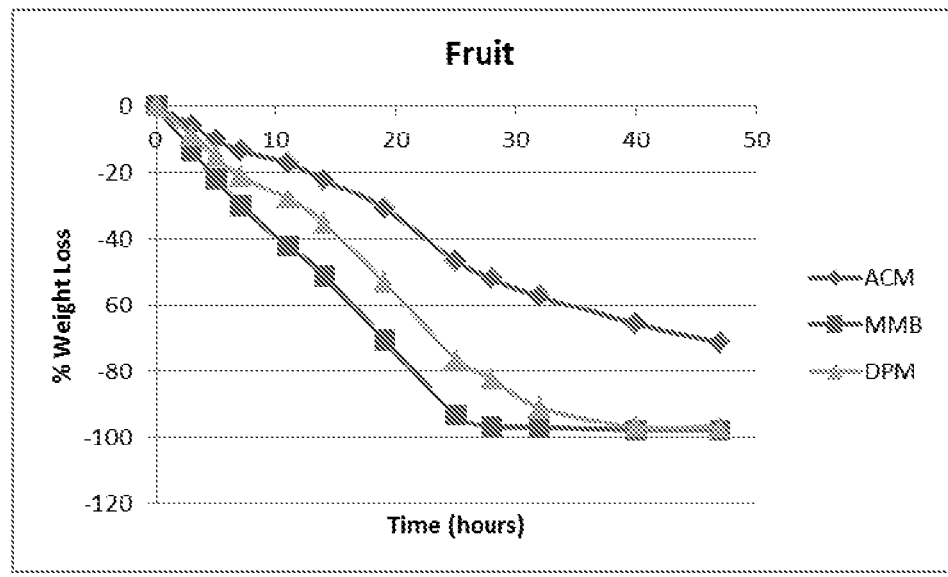
FIG. 3 is an evaporation comparison among Low VOC carrier formulations C1, C2, and C3, as described below in Example 3, measured as the amount of weight loss of fruit fragrance over 50 hours.
Figure 3:
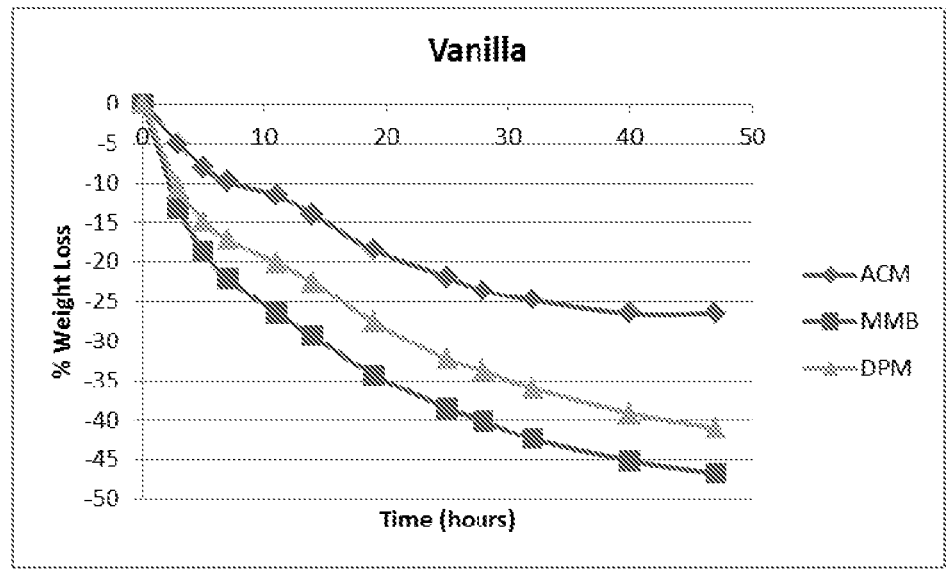

From the Evaporation curves shown in FIGS. 3 and 3*bis*, measured as the amount of weight loss of the composition, evaporation profile of the Low VOC Carrier Formulations C1 and C4 over 50 hours is better than of Comparative Formulations C2, C3, C5 and C6, which are not compliant with the regulations established by the California Air Resource Board (CARB). Indeed, Formulations C1 and C4 evaporate slower than Comparative Formulations C2, C3, C5 and C6, which means the solvent of C1 and C4 is able to carry the fragrance into the air for a longer period of time, showing better performance.

Example 4—Solvent Based Fragrance Compositions

Commercially-available fragrances are solubilized into the solvents described below in Table 4, and the evaporation rate is measured.

TABLE 4

Fragrance Composition for a Reed Diffuser (Wick Device Type).

| Components | D1 % w/w | D2 % w/w | D3 % w/w | D4 % w/w | D5 % w/w | D6 % w/w | D7 % w/w | D8 % w/w | D9 % w/w | D10 % w/w |
|---|---|---|---|---|---|---|---|---|---|---|
| Citrus Fragrance | 20 | 20 | 20 | 20 | 20 | 0 | 0 | 0 | 0 | 0 |
| Lavender Fragrance | 0 | 0 | 0 | 0 | 0 | 20 | 20 | 20 | 20 | 20 |
| Augeo Clean Multi | 0 | 40 | 40 | 0 | 0 | 0 | 40 | 40 | 0 | 0 |
| Augeo Clean Plus | 80 | 40 | 0 | 0 | 0 | 80 | 40 | 0 | 0 | 0 |
| Augeo ACT | 0 | 0 | 40 | 0 | 0 | 0 | 0 | 40 | 0 | 0 |
| Dowanol DPM (Glycol ether) | 0 | 0 | 0 | 80 | 0 | 0 | 0 | 0 | 80 | 0 |
| Methoxy methyl butanol | 0 | 0 | 0 | 0 | 80 | 0 | 0 | 0 | 0 | 80 |

Figure 4:
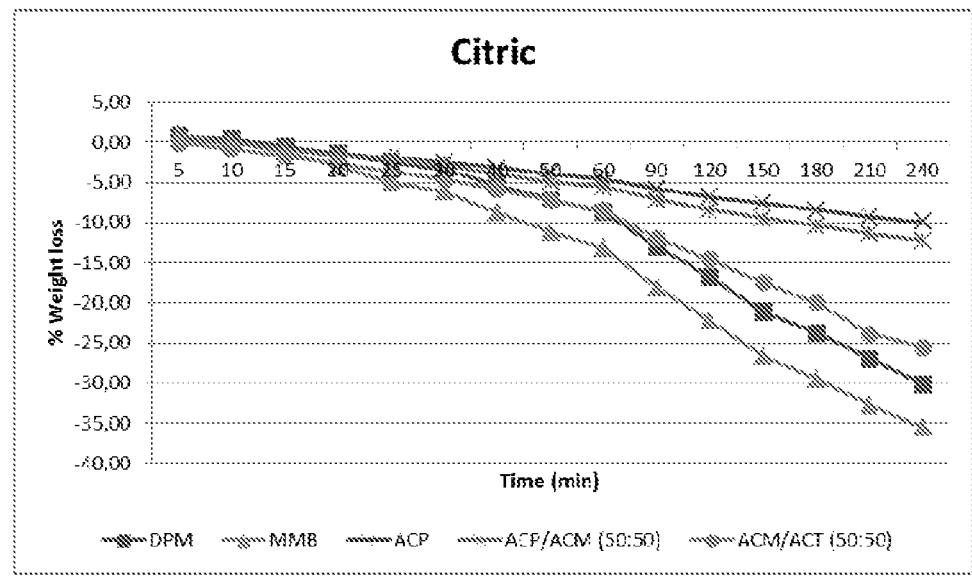
FIG. 4 is an evaporation comparison among Low VOC carrier formulations D1, D2, D3, D4, and D5, as described below in Example 4, measured as the amount of weight loss of citrus fragrance over 240 minutes.
Figure 4:
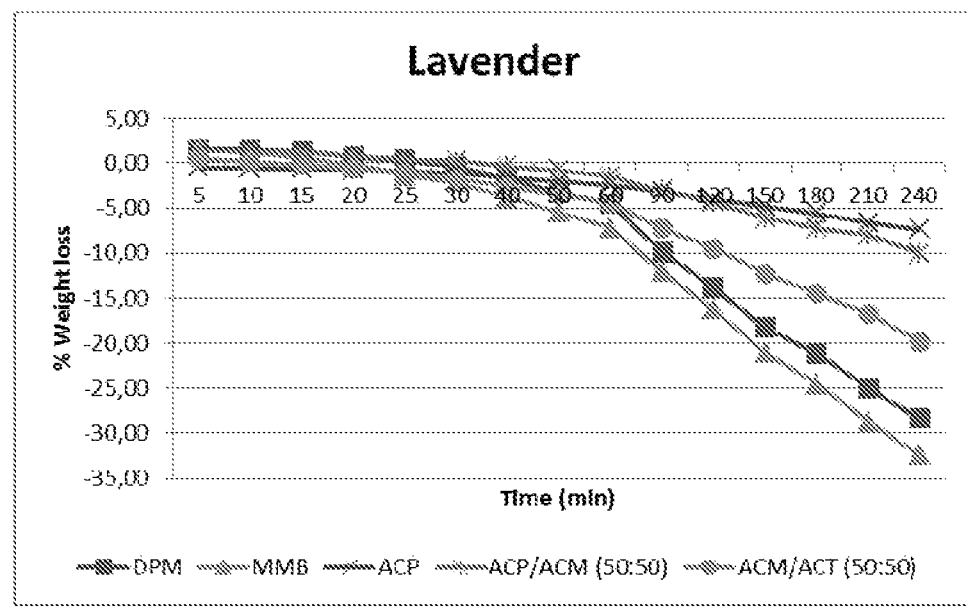

From the Evaporation curves shown in FIGS. 4 and 4*bis*, measured as the amount of weight loss of the composition, evaporation profile of the Low VOC Carrier Formulations D1 to D3 and D6 to D8 over 240 minutes is better than of Comparative Formulations D4 and D5 and D9 and D10, which are not compliant with the regulations established by the California Air Resource Board (CARB). Indeed, Formulations D1 to D3 and D6 to D8 evaporate slower than Comparative Formulations D4 and D5 and D9 and D10, which means the solvent of D1 to D3 and D6 to D8 is able to carry the fragrance into the air for a longer period of time, showing better performance.

Example 5—Water Based Fragrance Compositions

Fragrances compositions from commercially-available fragrances are prepared as described below in Table 5, and the evaporation rate is measured.

TABLE 5

Fragrance Composition for a Reed Diffuser (Wick Device Type).

| Components | E1 % w/w | E2 % w/w | E3 % w/w |
|---|---|---|---|
| Water (pH > 7.5) | 40 | 40 | 40 |
| Lavender Fragrance | 10 | 10 | 10 |
| Augeo Clean Multi | 50 | 0 | 0 |
| Dowanol DPM (Glycol ether) | 0 | 50 | 0 |
| Methoxy methyl butanol | 0 | 0 | 50 |

Figure 5:
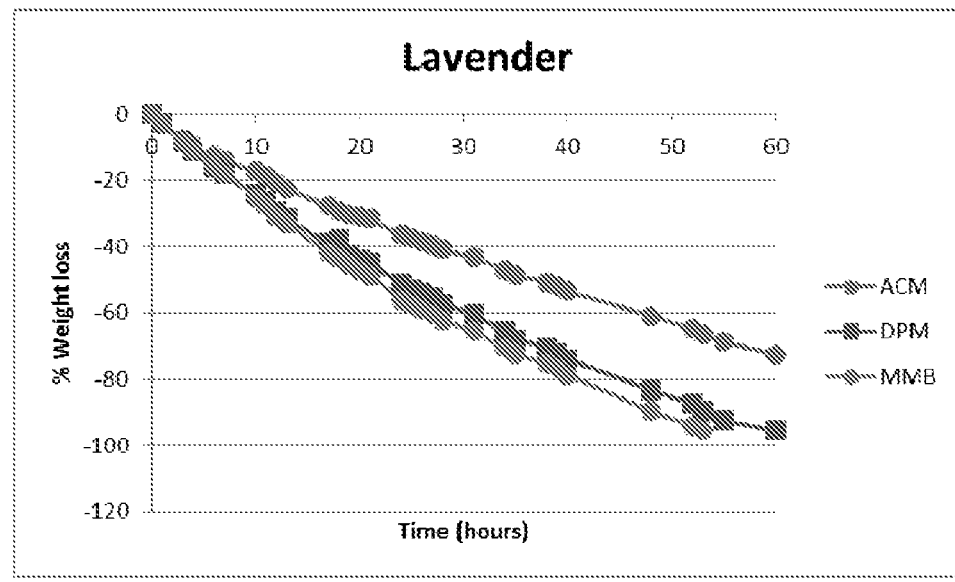
FIG. 5 is an evaporation comparison among Low VOC carrier formulations E1, E2, and E3, as described below in Example 5, measured as the amount of weight loss of lavender fragrance over 60 hours.

From the Evaporation curves shown in FIG. 5, measured as the amount of weight loss of the composition, evaporation profile of the Low VOC Carrier Formulation E1 over 50 hours is better than of Comparative Formulations E2 and E3, which are not compliant with the regulations established by the California Air Resource Board (CARB). Indeed, Formulation E1 evaporates slower than Comparative Formulations E2 and E3, which means the solvent of E1 is able to carry the fragrance into the air for a longer period of time, showing better performance.

Example 6—Water Based Fragrance Compositions

Fragrances compositions from commercially-available fragrances are prepared as described below in Table 6, and the evaporation rate is measured.

TABLE 6

Fragrance Composition for a Reed Diffuser (Wick Device Type).

| Components | F1 % w/w | F2 % w/w | F3 % w/w | F4 % w/w | F5 % w/w | F6 % w/w | F7 % w/w | F8 % w/w | F9 % w/w | F10 % w/w |
|---|---|---|---|---|---|---|---|---|---|---|
| Citrus Fragrance | 5 | 5 | 5 | 5 | 5 | 0 | 0 | 0 | 0 | 0 |
| Lavender Fragrance | 0 | 0 | 0 | 0 | 0 | 5 | 5 | 5 | 5 | 5 |
| Augeo Clean Multi | 0 | 10 | 10 | 0 | 0 | 0 | 10 | 10 | 0 | 0 |
| Augeo Clean Plus | 20 | 10 | 0 | 0 | 0 | 20 | 10 | 0 | 0 | 0 |
| Augeo ACT | 0 | 0 | 10 | 0 | 0 | 0 | 0 | 10 | 0 | 0 |

TABLE 6-continued

Fragrance Composition for a Reed Diffuser (Wick Device Type).

| Components | F1 % w/w | F2 % w/w | F3 % w/w | F4 % w/w | F5 % w/w | F6 % w/w | F7 % w/w | F8 % w/w | F9 % w/w | F10 % w/w |
|---|---|---|---|---|---|---|---|---|---|---|
| Dowanol DPM (Glycol ether) | 0 | 0 | 0 | 20 | 0 | 0 | 0 | 0 | 20 | 0 |
| Methoxy methyl butanol | 0 | 0 | 0 | 0 | 20 | 0 | 0 | 0 | 0 | 20 |
| Lauryl alcohol 7EO | 25 | 25 | 25 | 25 | 25 | 25 | 25 | 25 | 25 | 25 |
| Water (pH > 7.5) | 50 | 50 | 50 | 50 | 50 | 50 | 50 | 50 | 50 | 50 |

Figure 6:
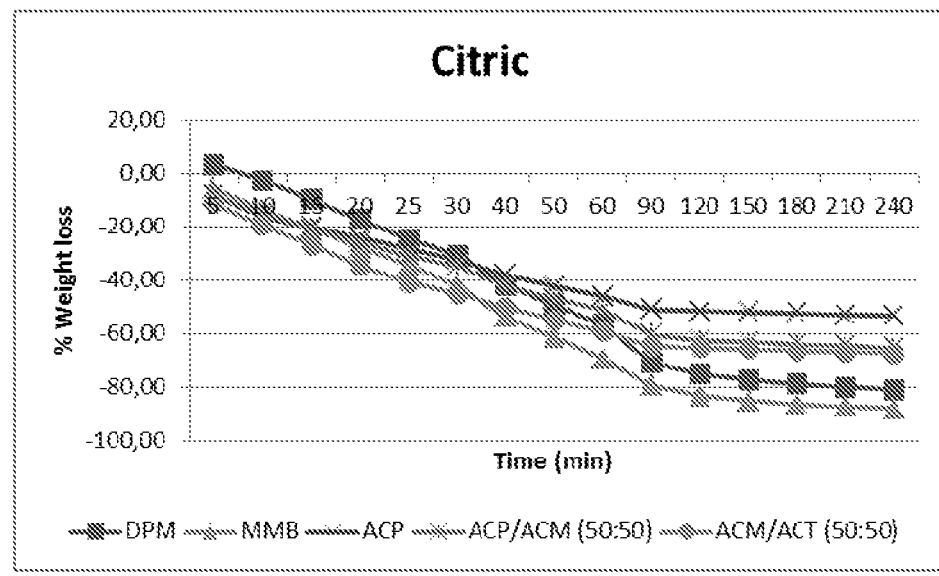
FIG. 6 is an evaporation comparison among Low VOC carrier formulations F1, F2, F3, F4, and F5, as described below in Example 6, measured as the amount of weight loss of citrus fragrance over 240 minutes.

From the Evaporation curves shown in FIGS. 6 and 6bis, measured as the amount of weight loss of the composition, evaporation profile of the Low VOC Carrier Formulations F1 to F3 and F6 to F8 over 240 minutes is better than of Comparative Formulations F4 and F5 and F9 and F10, which are not compliant with the regulations established by the California Air Resource Board (CARB). Indeed, Formulations F1 to F3 and F6 to F8 evaporate slower than Comparative Formulations F4 and F5 and F9 and F10, which means the solvent of F1 to F3 and F6 to F8 is able to carry the fragrance into the air for a longer period of time, showing better performance.

The use of such examples is illustrative only and in no way limits the scope and meaning of the invention or of any exemplified term or phrase used herein. Likewise, the invention is not limited to any particular preferred embodiments described herein. Indeed, many modifications and variations of the invention will be apparent to those skilled in the art upon reading this specification.

It is further to be understood that all values are approximate, and are provided for description.

The invention claimed is:

1. A fragrance composition, comprising a fragrance compound and a carrier, wherein the carrier comprises, in an amount of at least 10% by weight based on the total weight of the carrier, at least one compound according to formula I:

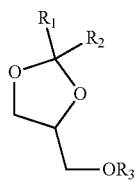

(I)

wherein:
$R_1$ and $R_2$ are each, independently from one another, selected from the group consisting of linear or branched C1-C12 alkyl, C4-C12 cycloalkyl, and aryl,
$R_3$ is H, linear or branched alkyl, cycloalkyl, or C(=O)$R_4$, and
$R_4$ is linear or branched alkyl or cycloalkyl,
wherein the fragrance composition comprises up to 50% by weight, based on the total weight of the composition, of water.

2. A fragrance composition as claimed in claim 1, wherein $R_1$ and $R_2$ are each, independently from one another, selected from the group consisting of methyl, ethyl, isopropyl, n-propyl, isobutyl, n-butyl, tert-butyl, n-pentyl, cyclopentyl, cyclohexyl, and phenyl.

3. A fragrance composition as claimed in claim 1, wherein $R_3$ is H or C(=O)$R_4$, and $R_4$ is methyl, ethyl, isopropyl, n-propyl, isobutyl, n-butyl, or tert-butyl.

4. A fragrance composition as claimed in claim 1, wherein $R_1$ and $R_2$ are each methyl and $R_3$ is H.

5. A fragrance composition as claimed in claim 1, wherein $R_1$ is methyl, $R_2$ is isobutyl, and $R_3$ is H.

6. A fragrance composition as claimed in claim 1, wherein $R_1$ is methyl, $R_2$ is phenyl, and $R_3$ is H.

7. A fragrance composition as claimed in claim 1, wherein $R_1$ and $R_2$ are methyl, $R_3$ is —C(=O)$R_4$, and $R_4$ is methyl.

8. A fragrance composition as claimed in claim 1, a blend of two or more compounds of formula I.

9. A fragrance composition as claimed in claim 8, wherein the blend comprises the following compounds I.1 and I.2:

(I.1)

(I.2)

10. A fragrance composition as claimed in claim 1, wherein the carrier comprises the at least one compound of formula I in an amount of at least 20% by weight, based on the total weight of the carrier.

11. A fragrance composition as claimed in claim 1, wherein the carrier comprises the compound of formula I in an amount of 100% by weight based on the total weight of the carrier.

12. A fragrance composition as claimed in claim 1, wherein the amount of the fragrance compound is from 10 to 80% by weight, based on the total weight of the fragrance composition.

13. A method for controlling evaporation of a fragrance composition that comprises a fragrance compound and one or more carriers, comprising as at least one of the one or more carriers at least one compound according to formula I:

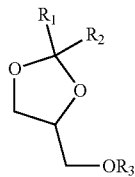

(I)

wherein
$R_1$ and $R_2$, independently from one another, are selected from the group consisting of linear or branched C1-C12 alkyl, C4-C12 cycloalkyl, and aryl,
$R_3$ is H, linear or branched alkyl, cycloalkyl or —C(=O) $R_4$ group, and
$R_4$ is a linear or branched alkyl or cycloalkyl,
in an amount of at least 10% by weight based on the total weight of the one or more carriers, wherein the fragrance composition comprises no greater than 50% by weight, based on the total weight of the composition, of water.

14. A method for controlling evaporation of a fragrance composition that comprises a fragrance compound and one or more carriers from an air care device selected from the group consisting of a wicking device, an electrical device, and an aerosol device, comprising including as at least one of the one or more carriers at least one compound according to formula I:

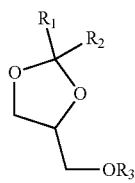

(I)

wherein
$R_1$ and $R_2$, independently from one another, are selected the group consisting of linear or branched C1-C12 alkyl, C4-C12 cycloalkyl and aryl,
$R_3$ is H, linear or branched alkyl, cycloalkyl or —C(=O) $R_4$ group, and
$R_4$ is linear or branched alkyl or cycloalkyl,
in an amount of at least 10% by weight based on the total weight of the one or more carriers, wherein the fragrance composition comprises no greater than 50% by weight, based on the total weight of the composition, of water.

15. An air care device comprising the fragrance composition of claim 1, wherein the air care device is a wicking device, an electrical device, or an aerosol device.

16. The air care device of claim 13, wherein the air care device is an electrical liquid air freshener.

17. The air care device of claim 13, wherein the air care device is a plug-in.

18. The air care device of claim 13, wherein the air care device is a reed diffuser.

19. A fragrance composition as claimed in claim 10, wherein the at least one compound of formula I represents at least 40% by weight, based on the total weight of carrier.

20. A fragrance composition as claimed in claim 10, wherein the at least one compound of formula I represents at least 60% by weight, based on the total weight of carrier.

21. A fragrance composition as claimed in claim 12, wherein the composition comprises from 20 to 60% by weight, based on the total weight of the fragrance composition, of the fragrance compound.

22. The composition of claim 1, wherein the fragrance composition comprises no greater than 40% by weight, based on the total weight of the composition, of water.

23. The composition of claim 1, wherein the fragrance composition comprises no greater than 20% by weight, based on the total weight of the composition, of water.

* * * * *